United States Patent [19]

Manoukian et al.

[11] Patent Number: 5,300,066

[45] Date of Patent: Apr. 5, 1994

[54] CONTACT LASER DELIVERY SYSTEM

[75] Inventors: Nubar Manoukian, Cupertino; James L. Hobart, Los Altos Hills; Kenneth Witte, San Jose, all of Calif.

[73] Assignee: Coherent, Inc., Palo Alto, Calif.

[21] Appl. No.: 905,125

[22] Filed: Jun. 23, 1992

Related U.S. Application Data

[63] Continuation of Ser. No. 584,287, Sep. 18, 1990, abandoned, which is a continuation-in-part of Ser. No. 577,866, Sep. 4, 1990, abandoned, which is a continuation-in-part of Ser. No. 477,256, Feb. 7, 1990, abandoned.

[51] Int. Cl.$^5$ .............................................. A61N 5/06
[52] U.S. Cl. .......................................... 606/15; 606/2; 606/17
[58] Field of Search ................................. 606/2-18

[56] References Cited

U.S. PATENT DOCUMENTS

| | | | |
|---|---|---|---|
| 3,693,623 | 9/1972 | Harte et al. ........................ | 606/9 |
| 3,843,865 | 10/1974 | Nath .................................. | 128/395 |
| 4,519,390 | 5/1985 | Horne ................................ | 606/15 |
| 4,576,177 | 3/1986 | Webster, Jr. ....................... | 606/17 |
| 4,660,925 | 4/1987 | McCaughan, Jr. ................. | 606/16 |
| 4,803,460 | 5/1989 | Goldenberg ....................... | 350/96.10 |
| 4,819,630 | 4/1989 | DeHart .............................. | 128/303.1 |
| 4,917,084 | 4/1990 | Sinofsky ............................ | 606/7 |
| 4,950,266 | 8/1990 | Sinofsky ............................ | 128/398 |

FOREIGN PATENT DOCUMENTS

| | | | |
|---|---|---|---|
| 0069565 | 1/1983 | European Pat. Off. | A61B 17/36 |
| 0181199 | 5/1986 | European Pat. Off. | A61B 17/36 |
| 2853528 | 6/1980 | Fed. Rep. of Germany | A61B 17/36 D |

*Primary Examiner*—David M. Shay
*Attorney, Agent, or Firm*—Limbach & Limbach

[57] ABSTRACT

A method and apparatus for minimizing damage to an optical fiber used as part of a laser radiation delivery system are disclosed. The apparatus includes the use of a spacer positioned adjacent the tip of the fiber to minimize the impact on the fiber tip of debris and vapor generated by exposure of a tissue target to high energy radiation. The end of the apparatus is configured to vent debris and vapor from the end of the tip to reduce damage. The fiber tip may also be annealed to enhance its resistance to damage. The buffer material may also be stripped from the delivery end of the fiber so that the inner diameter of the outer support can be narrowed. An epoxy resin is injected into the space between the uncoated fiber and the support to stabilize the fiber and prevent it from bending. The delivery end of the fiber can also be enlarged to shield the remainder of the fiber from debris and vapor.

6 Claims, 3 Drawing Sheets

CONTACT LASER DELIVERY SYSTEM

CROSS REFERENCE TO OTHER RELATED APPLICATIONS

This is a continuation of co-pending application Ser. No. 07/584,287 filed on Sep. 18, 1990, which is a Continuation-in-Part of application Ser. No. 07/577866, filed Sep. 4, 1990, which was in turn a Continuation-in-Part of application Ser. No. 07/477,256, filed Feb. 7, 1990, all now abandoned.

BACKGROUND OF THE INVENTION

This application relates to a novel optical fiber laser delivery system and the method of using the same. Such delivery systems are now used for certain types of surgery, such as arthroscopic surgery.

Laser radiation is used in surgical applications where the cutting of tissue is desired, or where the target tissue, such as a tumor, is to be destroyed. In such systems, various types of laser radiation have been used i.e. both continuous wavelength and pulsed, the radiation being passed through an optical fiber, and to the fiber tip. To achieve better cutting efficiency, the fiber tip is placed immediately adjacent the tissue target.

We have found that high energy pulsed laser radiation provides an effective means for such tissue destruction. For example, we have found that very effective delivery of radiation occurs where energies of two joules over a pulse of 350 microseconds are delivered at a frequency of ten hertz.

While the use of high energy pulsed radiation is effective for the destruction of tissue, we have found that catastrophic damage to the tip of the optical fiber carrying such radiation likewise occurs in many cases. Clearly, such damage is costly from a reliability standpoint. More importantly, failure of the fiber tip during surgery could lead to the deposit of debris from the destroyed tip in the patient's body.

Tip breakdown results from a number of mechanisms. For example, there may be inherent structural weaknesses arising from manufacture, such as microcracks and polishing or cleaving defects. More importantly, when sufficient laser power is delivered through a fiber to various types of tissue in a water or other medium, cutting is achieved by rapid vaporization of the water contained in the material. The resultant unbalanced pressure produces high velocity fragments which abrade and erode the materials used in the delivery device. In particular, we have found that the stainless steel and the glass components of the end piece are eroded at moderate rates, while other softer materials such as adhesives used in the manufacture of the handpiece and the fiber buffer erode much more rapidly.

Thus, it would be advantageous to provide a contact optical fiber laser delivery system for surgery wherein the delivery system was designed to minimize damage to the fiber tip arising from exposure to the forces generated when the fiber is used to transmit high energy laser radiation to the surface of the tissue in question.

It is well known with respect to fiber optics that a bare glass fiber has a very much lower tensile strength than a fiber which has been coated by a plastic. (The plastic coating is often called a buffer or "cladding.") In one particular example, we found that 480 micrometer diameter bare fibers broke when wrapped around a 5 centimeter diameter mandrill, while the same fibers when protected by a silicone buffer could be wrapped around a 2 centimeter mandrill without breakage.

In many applications of the laser in medicine, it is desirable to transmit the laser through a bent fiber in order to reach otherwise inaccessible locations. In order to reduce breakage of the fiber, it is thus desirable to have a buffer on the bent fiber. However, as noted above, the buffer material is subject to relatively fast erosion. Accordingly, it would be desirable to provide a probe which can be bent but which is not subject to rapid erosion.

SUMMARY OF THE INVENTION

In order to attain this advantage, the present invention includes a contact laser delivery method for exposing tissue to laser radiation but minimizing damage to the fiber tip, the method comprising the steps of providing an optical fiber having an end for directing that radiation at a tissue target, supporting the end of the optical fiber at a predetermined distance from the tissue target, and exposing the tissue target with the laser radiation delivered through the fiber, thereby vaporizing at least some tissue and creating debris.

The method of the invention may also include the step of mounting a spacer on the end of the fiber in order to achieve optimal spacing of the fiber tip from the tissue target. To minimize damage to the fiber tip, the method may also include the step of venting the debris and vapor away from the fiber tip.

In a preferred embodiment the method includes the step of providing the end of the fiber with a substantially planar annealed tip.

Additionally, the invention includes a contact laser delivery apparatus for exposing tissue to laser radiation comprising an optical fiber having an end for directing that radiation at a tissue target, and support means at the end of the optical fiber for supporting the end at a predetermined distance from the tissue target. Vent means for venting debris and vapor created by exposure of the tissue target to the radiation may also be used.

In one embodiment, the support means comprises a spacer positioned adjacent the fiber tip which extends outwardly therefrom, such that when the outermost end of the spacer is rested on the tissue target the fiber tip is held at a distance of from about 150 to about 500 micrometers from the tissue target.

In a further embodiment, the invention includes a contact laser delivery apparatus for exposing tissue to laser radiation comprising an optical fiber having a substantially planar end for directing laser radiation at a tissue target, wherein the substantially planar end of the fiber is annealed to improve structural stability and resistance to damage.

In still another embodiment of the subject invention, the buffer material used to increase the bending strength of the fiber is removed in a region adjacent the delivery end of the fiber. The inner diameter of the outer tubular member is reduced in this region. In addition, an adhesive fills the space between the uncoated fiber and the tubular member. Since the adhesive layer is much thinner than the buffer, it will be more resistant to erosion. In addition, the adhesive prevents the probe from being bent in the uncoated region. The probe is bent in the region which is coated.

In a further embodiment, the delivery end of the fiber is enlarged to shield the fiber from erosion.

BRIEF DESCRIPTION OF THE DRAWINGS

The invention will be better understood by reference to the attached figures of which.

DETAILED DESCRIPTION OF THE INVENTION

Figure 1:
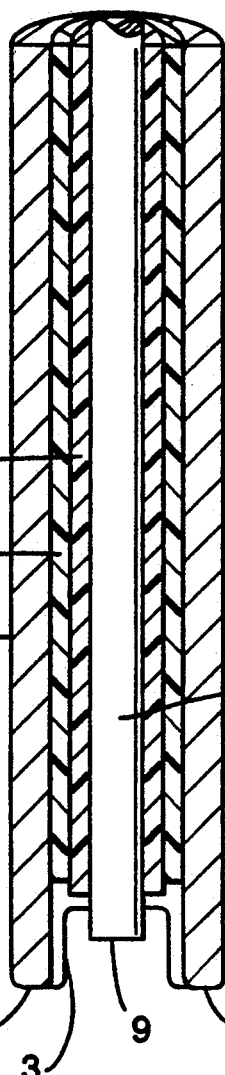
FIG. 1 is a side, partial cross-sectional view of the preferred embodiment of the apparatus of the invention showing the vented holder surrounding the optical fiber tip or end.

We have now found that it is feasible to reliably deliver high energy pulsed radiation through an optical fiber without damage to the fiber tip. Specifically, we have found that damage to the fiber tip can be avoided by annealing the fiber tip. By "annealing" it is meant that the fiber tip, which is cut and polished after formation of the melted and cooled fiber, is further subjected to a high temperature annealing process, including partial remelting, whereby stresses, microcracks and other weaknesses are relieved and reformed.

The following examples quantify the improved results achieved in this manner.

EXAMPLES

1. Comparative Example—Unprotected Fiber Tip in Water

An experiment was conducted by placing a 200 μm diameter cleaved fiber tip in water, to simulate the saline water environment under which most surgeries utilizing the invention occur. Radiation was delivered using a Ho:YAG laser at an average power of 13 watts and a repetition rate of 10 Hz.

In this example, nine fibers were tested, and catastrophic destruction of the tip occurred in approximately 70% of the cases after 3,000 pulses. It was found that the fiber tip typically broke parallel to the optical axis and that typically fragments of size of the order of 300 micrometers long were produced.

A similar experiment was run using a 400 micrometer diameter polished fiber. This fiber performed better but showed missing pieces of about 400 micrometers length after 4,000 pulses in about 40% of the cases. It should be noted that similar fiber destruction is observed when these fibers are used for tissue cutting under saline.

2. Example —Annealed Tip

In order to test whether damage could be minimized by use of an annealed tip, we compared damage occurring in untreated fiber tips with damage which occurred where the tip was annealed to relieve stress and surface discontinuities.

The conditions as in the comparative example above were used (cleaved 200 micrometer core diameter fiber made of low OH fused silica) but in the present case the fiber tip was annealed. In order to anneal the tip a two electrode fusion splicer (Orionics) was used to slowly bring the fiber tip to a white hot condition such that the tip was melted to a depth of approximately 20 microns. This process tends to smooth the corners or edges of the tip face. It is believed that this process acts to anneal the tip, thus minimizing stresses and strains present in the tip.

Subsequently, the fiber tip was placed in water and 3,000 pulses of radiation (15 watts, 10 Hz) Were applied.

Five such fibers were initially tested, and no damage at all was observed. Thus, this experiment shows a surprising 0% failure rate by use of the annealed fiber tip. Subsequent experiments testing over 40 fibers under similar conditions confirm that the use of an annealed and partially remelted tip assures that no damage to the fiber tip occurs when the fiber is used in water. This result is particularly encouraging when compared with the result in Comparative Example 1, where the fiber tip showed such a high frequency of catastrophic damage.

While these experiments were conducted using pulsed radiation, it is believed that this process will be effective to ensure fiber tip stability under any circumstances in which high energy radiation which might cause tip damage is being used, whether that radiation is pulsed or continuous wavelength.

While it is known to produce so-called "lens-ended" fibers for use in some medical applications using certain high temperature techniques, we have found no description relating to annealing tips for imparting superior resistance to damage as in the present invention. As described in Russo et al., "Lens-ended Fibers for Medical Applications: A New Fabrication Technique" (Applied Optics, October 1984), bulb shaped, spherical arc shaped and elliptical arc shaped fiber tips may act as microlenses to improve the power density delivered to a tissue target. A number of methods for forming the lens, including heating of the tip by use of a microtorch, are discussed. The development of such lens-ended fibers has not directly addressed the problems of fiber tip breakdown, however. In fact, it has been found that such lens-ended fibers have increased susceptibility to damage from debris created when the tip is placed adjacent the tissue target during operation.

Unlike such art we have found that it is preferred to maintain the fiber tip in a substantially planer orientation so as to maximize tip strength. Shapes suitable for use as lenses tend to be more easily damaged than the substantially planer configuration. It is therefore preferred that a substantially planer annealed tip be used in the present invention.

Although the problem illustrated by Example 1 was substantially addressed by the above method of tip annealing, further problems were observed when the tips were used to vaporize actual tissue. The following example illustrates this problem.

3. Comparative Example —Unprotected Fiber Tip at the Tissue Surface

Standard practice has been to position the tip of an optical fiber directly adjacent the tissue being radiated for maximum effectiveness. To determine the degree of fiber damage under these conditions, a fused silica optical fiber having a core diameter of 200 micrometers was tested by placing the fiber tip directly adjacent tissue (cow meniscus) and firing the laser. This fiber had been subjected to the above tip annealing technique and performed without damage in a saline environment in the absence of tissue.

Damage in the form of a conical depression in the face of the fiber was observed. The depth of the cone increased with the number of "shots" carried through the fiber. For example, using radiation from a pulse Ho:YAG laser at an average power of 13 watts and a repetition rate of 10 Hz, it was found that a cone of about 220 micrometers in depth was formed on the fiber tip at 3,000 shots, and a cone depth of about 425 micrometers was formed at 6,000 shots. In addition to damage to the tip in the cone shape, other pitting and cracking of the tip occurred.

It is theorized that debris and vapor created due to the explosive laser ablation of tissue were causing this damage. Tests were run using an explosive ablation model to determine the expected relative density of impacts to the fiber tip face at various distances from the target tissue.

The results indicated that the density of particles expected to impact the face of the tip decreased substantially at the point where the fiber tip is held at a particular distance from the tissue target, as shown in the following Table.

TABLE

| DISTANCE (RADIUS UNITS) | EXPECTED RELATIVE IMPACT DENSITY |
|---|---|
| 0.5 | 4 |
| 0.6 | 2.8 |
| 0.7 | 2.1 |
| 0.8 | 1.6 |
| 0.9 | 1.25 |
| 1.0 | 1 |
| 1.5 | 0.5 |
| 2.5 | 0.25 |
| 3.5 | 0.20 |

As can be seen, we found that the expected density of particles impacting the tip face increases by a factor of approximately eight going from a spacing of one-half fiber core radius from the target to a distance of one and one-half times the fiber core radius.

This result indicated that damage should decrease as a function of separation distance, if damage to the tip was, in fact, a strong function of the explosive forces generated, as opposed to thermal and other forces which come into play. The distance at which the fiber tip is held from the target in order to minimize damage, however, must be balanced with the need for satisfactory transmission of the laser radiation to the target, usually through an absorbing saline solution. Thus, it was unclear whether a laser delivery system could be made to operate with any practical degree of efficiency when used at a distance from a tissue target which would significantly lower the exposure of the fiber tip to damage.

We surprisingly found, however, that distances from about 150 micrometers to about 500 micrometers provide a good balance of protection and radiation efficiency, where a pulsed Ho:YAG 2.1 micrometer wavelength laser is used with a fused silica low OH fiber having an annealed tip and a core diameter of from 200 to 600 microns and a cladding thickness of from 40 to 100 microns. As a practical limit we found it preferable to operate in the range of separation distances from 200 to 400 microns, since, at 400 microns absorption of the water began to affect the energy reaching the fiber tip. We also found that no damage to the fiber tip occurred for separation distances over 200 microns. It should be kept in mind, however, that the distance by which the fiber tip is separated from the target may vary even outside this range depending on factors such as fiber type, fiber size, radiation intensity and type, and even tissue type.

In order to achieve the preferred separation of fiber tip from target tissue, the holder or probe depicted in the attached drawings has been developed. Referring now to FIG. 1, a fiber support means, generally designated 1, is shown. At the tip of support means 1 groove or vent 3 is formed between outermost tips 5. Optical fiber 7 is shown held within support means 1, and spaced inwardly from outermost points 5 such that when points 5 are rested on target tissue (see FIG. 2), fiber tip 9 of fiber 7 will be supported at a predetermined distance from that target, thereby forming a vented spacer. Fiber tip 9 may be annealed, as described in detail previously, to enhance its strength.

At the other end of the fiber (not shown) laser radiation is coupled into the fiber. Many types of laser radiation can be used in the invention, the type chosen being dictated by its ability to perform as a part of a "laser scalpel," rather than any particular requirement of the present invention.

Those skilled in the present art will be familiar with the mounting of fiber 7 within a holder as is previously known. It is noted, however, that in the present invention, the fiber is surrounded by silicone buffer layer 11 and nylon jacket 13. Stainless steel tube 15 surrounds nylon layer 13.

It will likewise be recognized that support for the fiber tip at a predetermined distance from the target may be achieved using other housing materials and in many other ways. For example, it would be possible to use a gas stream having relatively high pressure through a concentric channel surrounding the fiber to provide both support for the fiber tip and a stream which would further inhibit the vapor and debris formed by the laser radiation from impacting the fiber tip.

Figure 2:
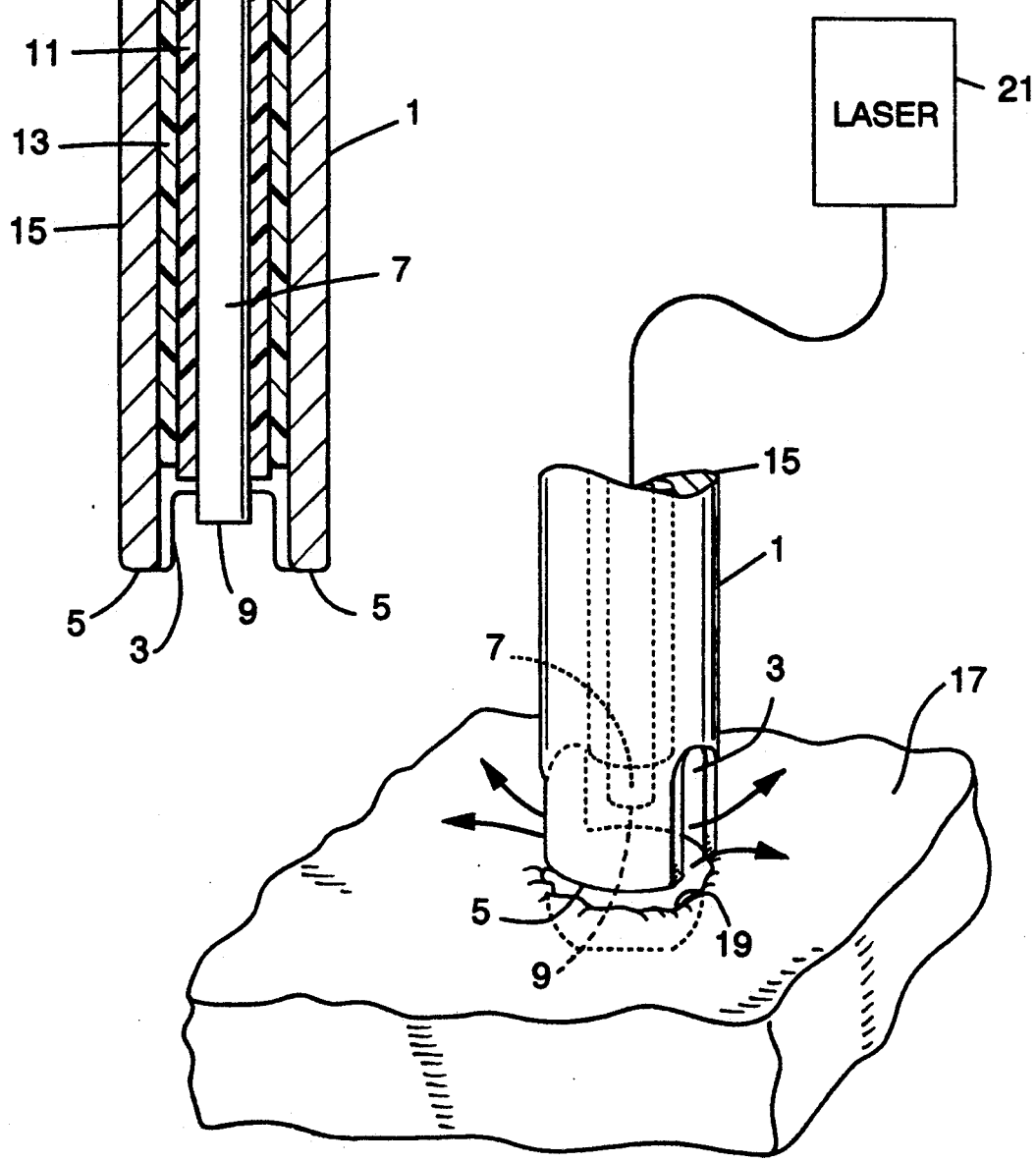
FIG. 2 is a perspective view of the vented holder in use, indicating how the debris and vapor are vented away from the tip of the optical fiber in use.

FIG. 2 shows support means 1 of FIG. 1 in use adjacent tissue target 17. As the laser radiation from laser 21 impacts target 17, cavity 19 is formed as the tissue and solution surrounding the tissue are vaporized. Such vapor and the debris carried with it may exit (arrows) through grooves 3 on either side of the tip without impacting the fiber tip. Thus, the receded tip arrangement of the invention not only minimizes damage resulting from acoustical and, perhaps, thermal shock, the debris and vapor which can cause additional damage are also vented to further minimize damage.

As mentioned previously, this venting may be enhanced by use of a relatively high pressure gas stream running through, for example, an annular space surrounding the fiber tip and exiting grooves 3.

Figure 3:
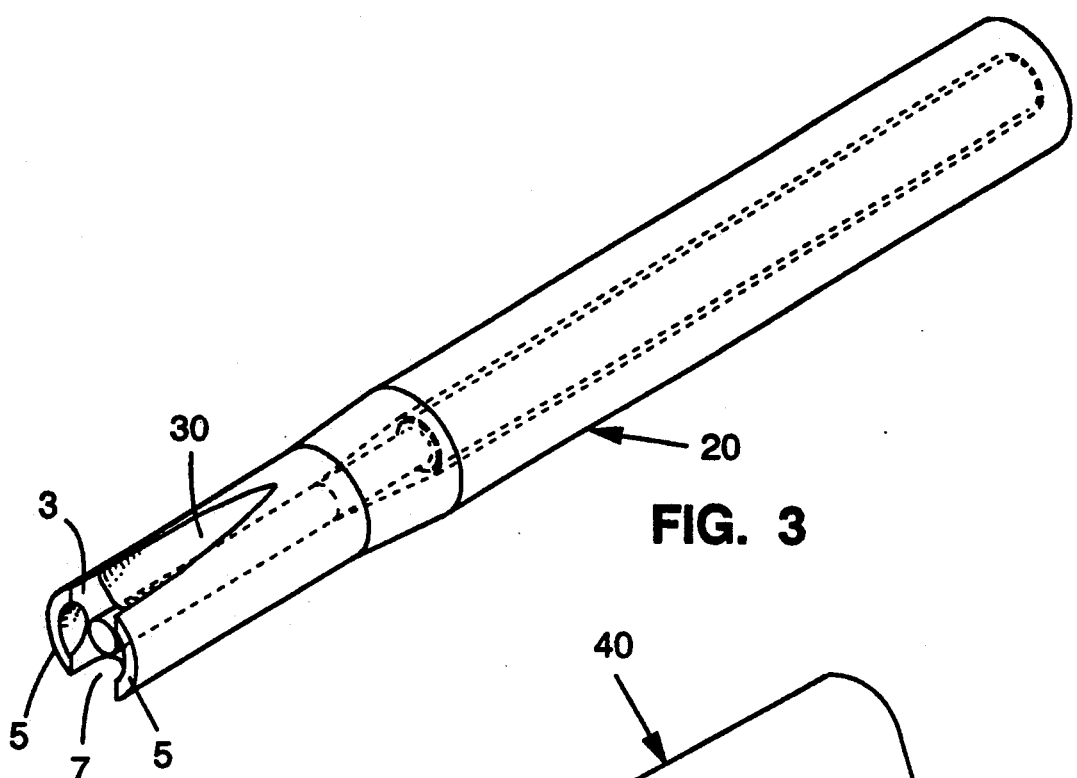
FIG. 3 is a perspective view of a second embodiment of the subject invention.

Turning to FIG. 3 there is illustrated a second embodiment of the holder or probe 20 of the subject invention. The internal structure of this embodiment can be the same as in the first embodiment.

The principle difference in the second embodiment is the addition of a pair of opposed, axially extending channels 30. The channels are provided to further enhance the venting action discussed above. In this manner, vapor and debris which can damage the delivery end of the fiber 7 can be more effectively removed.

The channels 30 can be used in combination with the groove 3 as shown in FIG. 3. Alternatively, the channels 30 could be used alone. Depending upon the procedures used and the effectiveness of the venting system, it may not be necessary to space the delivery end of the fiber away from the target tissue.

It is believed that the enhanced venting design shown in FIG. 3 will allow the probe to be used in situations where contact with the target tissue is increased. For example, this design could allow the probe to be used to drill holes in tissue where problems with damage from debris is greater than when the probe is used for incisions.

Figure 4:
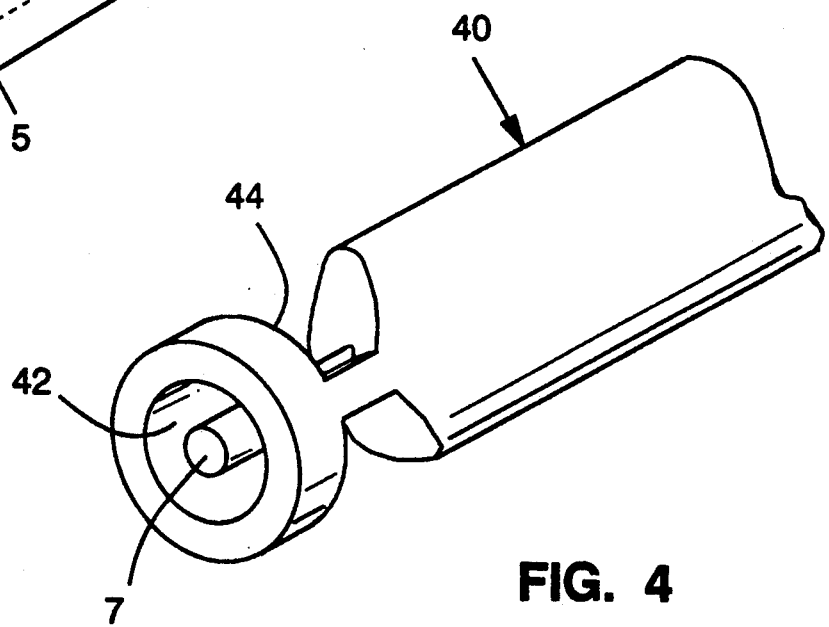
FIG. 4 is a perspective view of a third embodiment of the subject invention.
Figure 5:
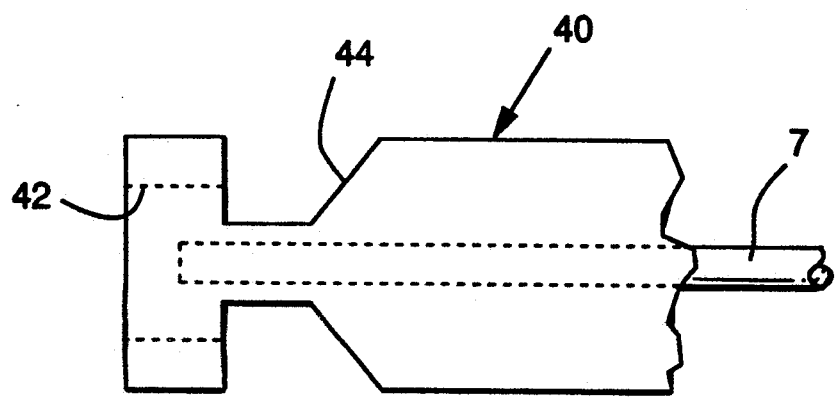
FIG. 5 is a side view of the third embodiment.

FIGS. 4 and 5 illustrate a third embodiment of the holder 40 of the subject invention. As in the first two embodiments, the fiber 7 is spaced from the end of the holder. In this embodiment, the venting means includes an annular channel 42 located at the distal end of the holder. In addition, a circumferential channel 44 is provided in the holder, spaced from the delivery end thereof. As in the second embodiment, it is believed that this configuration will provide enhanced venting of debris and vapor. As can be appreciated, it would be possible to employ other channelling structures which provide the necessary venting characteristics.

Figure 6:
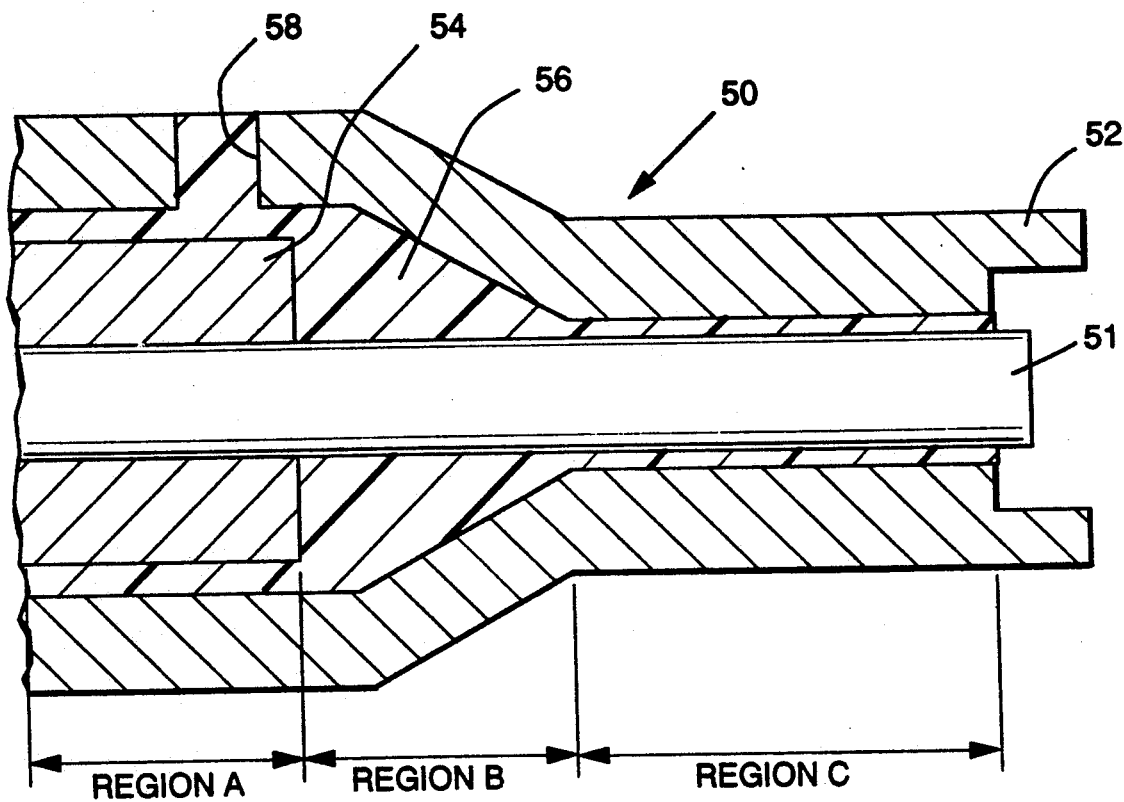
FIG. 6 is a cross sectional view of a fourth embodiment of the subject invention.

Turning to FIG. 6, there is illustrated a fourth embodiment of the subject invention also designed to minimizing erosion of the fiber optic material. As in the previous embodiments, the probe 50 includes a glass fiber 51 surrounded and supported by a stainless steel tubular member 52.

As noted above, the glass fiber is typically surrounded by a buffer 54 formed from a material such as silicon. The buffer material is provided to strengthen the fiber which it allows it to be bent during assembly of the probe. The buffer layer is relatively thick, on the order of 100 microns. Unfortunately, this material erodes rather quickly from debris and vapor during surgery. When this erosion occurs, the end of the fiber is free to move within the stainless steel support and breaks down.

In order to overcome this problem, it would be desirable to minimize the spacing between the outer diameter of the fiber and the inner diameter of the tubular support. In order to achieve this goal, the buffer material 54 is stripped away from the glass fiber in a region at the delivery end thereof. In the illustrated embodiment, the buffer is stripped back a distance of about 0.25 inches. The inner diameter of the support 52 is then reduced so that the spacing between the outer circumferential surface of the fiber and the inner circumferential surface of the support is very narrow. In the preferred embodiment this spacing is on the order of 0.0005 inches.

This structure is highly resistant to erosion. However, the region of the fiber which is uncoated with the buffer will be much more likely to break when the probe is bent during manufacturing. To overcome this problem, an adhesive 56 is injected into the probe so that it fills or encapsulates the space between the fiber and the support. The adhesive 56 is of the type which will not bend. Suitable adhesives are available and have been used to assemble probes. For example, we have used EPO-TEK 353 ND, epoxy resin manufactured by Epoxy Technology.

While the adhesive prevents the tip from being bent, the remainder of the probe can be bent during manufacturing to the desired angle. The elimination of flexibility in the tip should not prevent the assembly of probes with a variety of bend angles.

As illustrated in FIG. 6, the adhesive exists in three regions within the end of the probe. Preferably the adhesive is injected into an area that extends somewhat into region A that is coated with the buffer. In the preferred embodiment, the overlap region will be about 0.125 inches. The adhesive can be injected through a hole 58 provided in the support 52.

It is desirable to have the adhesive in region A because it fully fills the gap between the buffer and the support. This gap tends to be variable because of variations in the diameters of the support and the fiber (each having tolerances of several mils) as well as uncontrolled centration of the fiber within the support. If the gap is present, the fiber tends to get pushed toward one side of the support when the probe is bent which puts lateral stress on the fiber, possibly in an uncoated region. By filling the gap with adhesive, this problem is avoided. It is also desirable to fill region B where the transition to the uncoated fiber occurs and the inner diameter of the support is reduced to further reduce stress in the fiber.

In addition to preventing bending, the adhesive in region C also restrains the lateral movement of the fiber which is induced from either direct contact with the tissue being cut or forces created by the vaporization of water and tissue during each laser pulse. The encapsulation also prevents water and water vapor from penetrating into the fiber which reduces fiber strength.

The structure used in FIG. 6 can be used alone or in combination with the other improvements discussed above. For example, the support could extend beyond the delivery end of the fiber. In addition, the delivery end of the fiber can be annealed. Further, the support can include a configuration which enhances venting. In the preferred embodiment, all of these features are incorporated in the probe.

Figure 7:
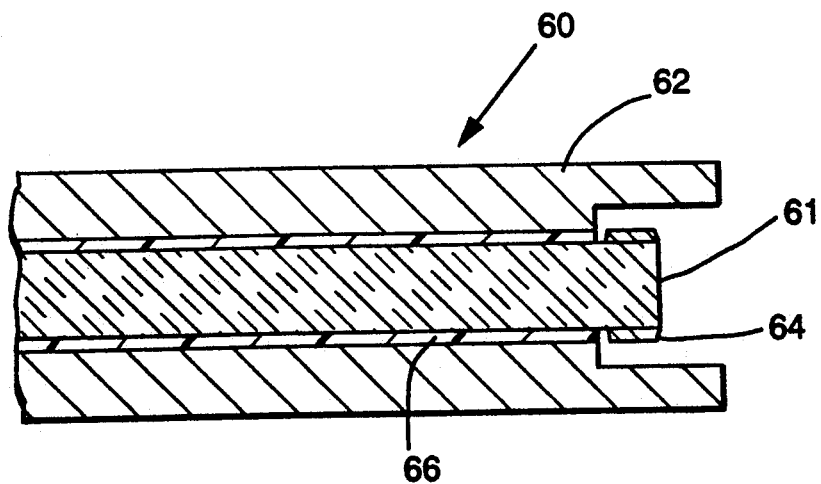
FIG. 7 is a cross sectional view of a fifth embodiment of the subject invention.

An additional approach to reducing damage from erosion is shown in the fifth embodiment of the probe 60 illustrated in FIG. 7. As noted above, the most rapid erosion occurs between the fiber 61 and the support 62. Accordingly, in this embodiment, the diameter of the end of the fiber 61 is enlarged to shield the area immediately behind the enlargement from debris and vapor. This enlargement can be produced in a variety of ways. For example, the enlargement could be formed in the arc of a fiber fusion machine. In the alternative, a separate sleeve 64 of erosion resistant material, such as glass could be added to the fiber. This approach for reducing erosion can also be used alone, or in conjunction with the other approaches discussed above. For example, a thin layer of adhesive 66 can be injected in the narrow space between an uncoated fiber and the support.

While only five embodiments of the invention have been described herein, many variations, including other holder designs which allow the fiber tip to be held at a predetermined distance from the target tissue or which provide an annealed tip by a process other than the application of high temperature to the fiber tip, or which provide alternate approaches for venting debris or which improve the erosion resistance characteristics of the probe are possible without departing from the true scope and spirit of the invention. It is intended that such variations come within the scope of the appended claims.

What is claimed is:

1. A fiber optic probe comprising:
   an optical fiber having a delivery end, said optical fiber having an outer coating of a buffer material to facilitate bending, with a region of said fiber extending from said delivery end being uncoated with said buffer material;

a tubular member surrounding and supporting said fiber while leaving said delivery end exposed, with the outer surface of the tubular member defining the outer surface of the probe and with the inner diameter of the tubular member being reduced in a portion of the area surrounding the uncoated region of said fiber to provide added support for the fiber and minimize the exposure of the fiber to debris and vapor; and an adhesive completely filling the area between said fiber and the reduced diameter region of said tubular member, said adhesive for prohibiting the flexing of the probe and reducing damage to the fiber from debris and vapor.

2. A fiber optic probe as recited in claim 1 wherein said adhesive is an epoxy resin.

3. A fiber optic probe as recited in claim 1 wherein the spacing between the inner surface of the reduced diameter region of the tubular member and the outer diameter of the fiber in the uncoated region is on the order of 0.0005 inches.

4. A fiber optic probe as recited in claim 1 wherein said adhesive extends to a point distal form the delivery end of the fiber, said point being beyond said uncoated region and the reduced diameter region of the tubular member.

5. A fiber optic probe as recited in claim 4 wherein said tubular member includes a opening for injection of said adhesive material.

6. A fiber optic probe as recited in claim 5 wherein said opening is located at a point spaced from said delivery end and beyond said uncoated region.

* * * * *